(12) United States Patent
Lin

(10) Patent No.: US 6,569,168 B2
(45) Date of Patent: May 27, 2003

(54) INTERVERTEBRAL DISTRACTOR AND IMPLANT INSERTION INSTRUMENT

(75) Inventor: Jo-Wen Lin, Tinton Falls, NJ (US)

(73) Assignee: Osteotech, Inc., Eatontown, NJ (US)

( * ) Notice: Subject to any disclaimer, the term of this patent is extended or adjusted under 35 U.S.C. 154(b) by 15 days.

(21) Appl. No.: 09/850,494

(22) Filed: May 7, 2001

(65) Prior Publication Data

US 2002/0010473 A1 Jan. 24, 2002

Related U.S. Application Data (60) Provisional application No. 60/202,225, filed on May 5, 2000.

(51) Int. Cl.$^7$ ................................. A61B 17/56
(52) U.S. Cl. ............................. 606/99; 600/201
(58) Field of Search ............... 606/90, 99, 105; 600/201, 214, 219, 235

(56) References Cited

U.S. PATENT DOCUMENTS

| | | | |
|---|---|---|---|
| 4,156,424 A | * | 5/1979 | Burgin ................ 600/212 |
| 4,545,374 A | | 10/1985 | Jacobson |
| D291,729 S | | 9/1987 | Greig |
| 4,878,915 A | | 11/1989 | Brantigan |
| 4,898,161 A | * | 2/1990 | Grundei ................ 606/105 |
| 4,997,434 A | | 3/1991 | Seedhom et al. |
| 5,059,194 A | | 10/1991 | Michelson |
| 5,122,130 A | | 6/1992 | Keller |
| 5,423,825 A | | 6/1995 | Levine |
| 5,431,658 A | | 7/1995 | Moskovich |
| 5,484,437 A | | 1/1996 | Michelson |
| 5,489,307 A | | 2/1996 | Kuslich et al. |
| 5,505,732 A | | 4/1996 | Michelson |
| D374,283 S | | 10/1996 | Michelson |
| 5,562,736 A | | 10/1996 | Ray et al. |
| 5,569,262 A | | 10/1996 | Carney |
| D377,093 S | | 12/1996 | Michelson |
| 5,658,336 A | | 8/1997 | Pisharodi |
| 5,697,977 A | | 12/1997 | Pisharodi |
| 5,700,291 A | | 12/1997 | Kuslich et al. |
| 5,704,937 A | | 1/1998 | Martin |
| 5,722,977 A | | 3/1998 | Wilhelmy |
| 5,741,253 A | | 4/1998 | Michelson |
| 5,772,661 A | | 6/1998 | Michelson |
| 5,797,909 A | | 8/1998 | Michelson |
| 5,797,917 A | | 8/1998 | Boyd et al. |
| D401,335 S | | 11/1998 | Koros et al. |
| 5,836,948 A | | 11/1998 | Zucherman et al. |
| 5,860,977 A | | 1/1999 | Zucherman et al. |
| 5,876,404 A | | 3/1999 | Zucherman et al. |
| 5,885,299 A | | 3/1999 | Winslow et al. |
| 5,899,901 A | | 5/1999 | Middleton |
| 5,928,139 A | * | 7/1999 | Koros et al. ............ 600/205 |
| 5,989,250 A | | 11/1999 | Wagner et al. |
| 6,004,326 A | | 12/1999 | Castro et al. |
| 6,017,342 A | | 1/2000 | Rinner |
| 6,024,696 A | * | 2/2000 | Hoftman et al. ............ 600/224 |
| 6,033,405 A | | 3/2000 | Winslow et al. |
| 6,042,582 A | | 3/2000 | Ray |
| 6,048,342 A | | 4/2000 | Zucherman et al. |
| 6,478,800 B1 | * | 11/2002 | Fraser et al. ................ 606/99 |

* cited by examiner

Primary Examiner—Ralph A. Lewis
Assistant Examiner—Michael B. Priddy
(74) Attorney, Agent, or Firm—Dilworth & Barrese, LI (57) ABSTRACT

A distractor/guide sleeve assembly is provided which includes a body having a cylindrical throughbore and a distractor assembly mounted thereon. The distractor assembly includes a rotatable dial, a pair of distractor rods, and two pairs of jaws. A plate is secured to the distal end of each distractor rod. Each plate includes a plurality of cam members which are slidably positioned in cam slots formed in the jaws of each of the pairs of jaws. The dial is operably connected to the jaws via the distractor rods such that rotation of the dial effects movement of the pairs of jaws between approximated and distracted positions. An insertion tool is also provided which includes a handle and distal engaging structure for releasably engaging an implant. The engaging structure includes a pair of prongs or protrusions having a slip resistant outer surface. The prongs are configured to be releasably received within correspondingly shaped bores formed in an implant.

11 Claims, 10 Drawing Sheets

INTERVERTEBRAL DISTRACTOR AND IMPLANT INSERTION INSTRUMENT

This application claims priority from Provisional Application Serial No. 60/202,225 filed May 5, 2000 and is hereby incorporated by reference.

BACKGROUND

1. Technical Field

The present disclosure relates generally to instrumentation for inserting an implant into a body receiving bed. More particularly, the present disclosure relates to instrumentation for guiding and positioning a dowel into a receiving bed formed in an intervertebral space.

2. Background to Related Art

Distractors and guide sleeves for positioning an implant into a receiving bed in the intervertebral space are well known. These distractors include forceps type distractorS as well as wedge type distractors which are pushed into the intervertebral space and distract upon insertion. The guide sleeve typically includes a cylindrical sleeve which is mounted to the adjacent vertebrae such that the instruments and implant can be positioned in the intervertebral space through the cylindrical sleeve. At least with respect to wedge type distractors, distraction of the vertebrae occurs unevenly with the front face of the vertebrae being distracted first. This is not desirable.

Accordingly, a need exists for an improved distractor/guide sleeve assembly which includes a simple integral assembly and provides for uniform distraction of adjacent vertebrae. A need also exists for an insertion tool useable with the distractor/guide sleeve assembly for inserting an implant into the intervertebral space.

SUMMARY

In accordance with the present disclosure, a distractor/guide sleeve assembly is provided which includes a body having a cylindrical throughbore and a distractor assembly mounted thereon. The distractor assembly includes a rotatable dial, a pair of distractor rods, and two pairs of jaws. A plate is secured to the distal end of each distractor rod. Each plate includes a plurality of cam members which are slidably positioned in cam slots formed in the jaws of each of the pairs of jaws. The dial is operably connected to the distractor rods such that rotation of the dial effects axial movement of the distractor rods. Axial movement of the distractor rods cause corresponding movement of each of the plates to move the cam members within the cam slots formed in each of the jaws. Movement of the cam members within the cam slots effects movement of each of the pairs of jaws between approximated and distracted positions.

An insertion tool is also provided which includes a handle and distal engaging structure for releasably engaging an implant. The engaging structure includes a pair of prongs or protrusions having a slip resistant outer surface. The prongs are configured to be releasably received within correspondingly shaped bores formed in an implant.

BRIEF DESCRIPTION OF THE DRAWINGS

Various preferred embodiments of the presently disclosed distractor/guide sleeve assembly are described herein with reference to the drawings, wherein.

DETAILED DESCRIPTION OF PREFERRED EMBODIMENTS

Preferred embodiments of the presently disclosed distractor/guide sleeve assembly will now be described in detail with reference to the drawings in which like reference numerals designate identical or corresponding elements in each of the several views.

Figure 1:
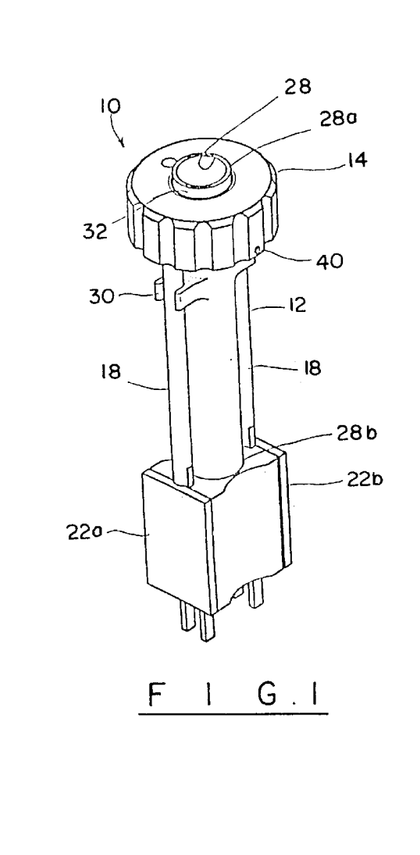
FIG. 1 is a perspective view of one preferred embodiment of the presently disclosed distractor/guide sleeve assembly.
Figure 1A:
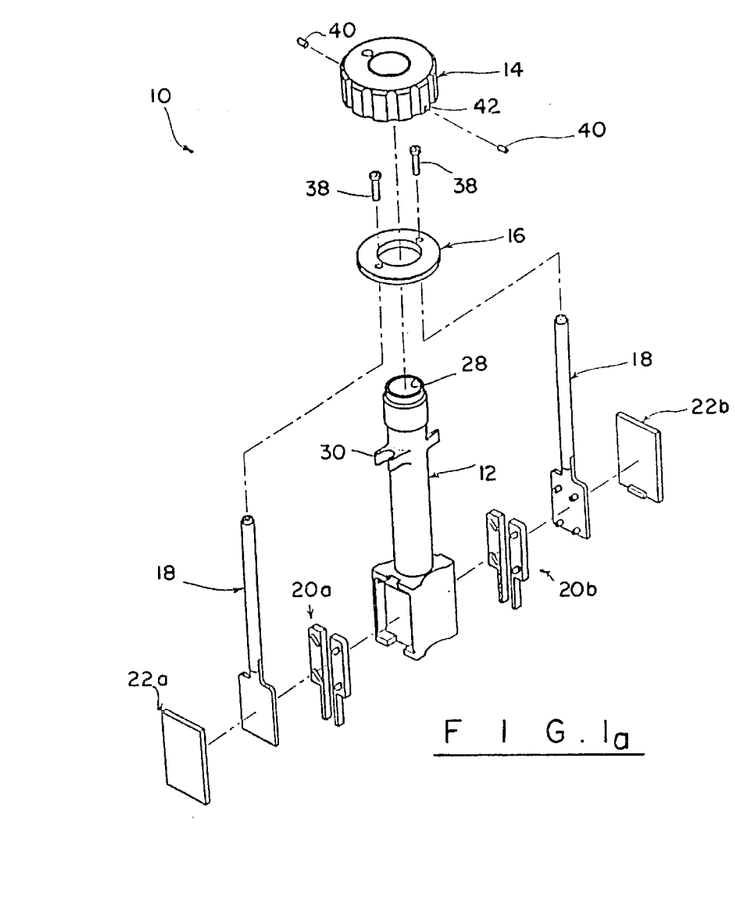
FIG. 1A is a perspective view with parts separated of the distractor/guide sleeve assembly shown in FIG. 1.

FIGS. 1 and 1A illustrate perspective views of the presently disclosed distractor/guide sleeve assembly, which is shown generally as 10. Distractor/guide sleeve assembly 10 includes a body 12, a rotatable dial 14, a ring 16, a pair of distractor rods 18, two pairs of jaws 20*a* and 20*b* and a pair of cover plates 22*a* and 22*b*. As will be described in greater detail below, dial 14 is rotatable to retract or advance distractor rods 18 to effect opening and closing, i.e., of each pair of jaws 20*a* and 20*b*.

Figure 2:
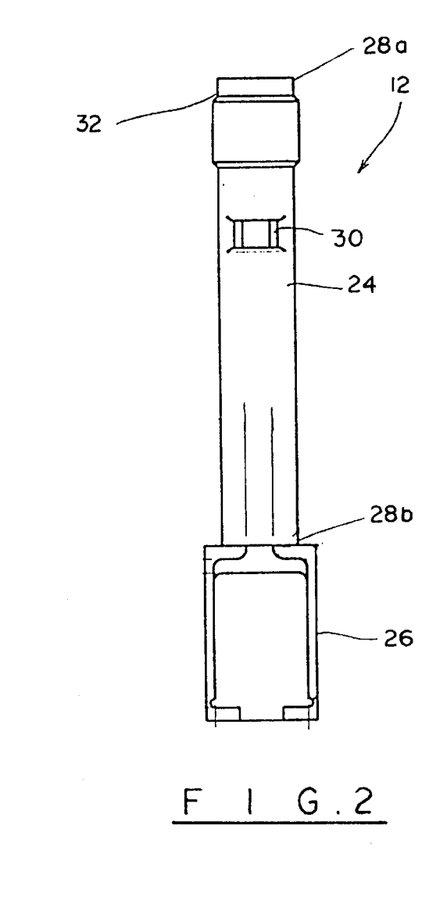
FIG. 2 is a side view of the distractor/guide sleeve assembly shown in FIG. 1.
Figure 2A:
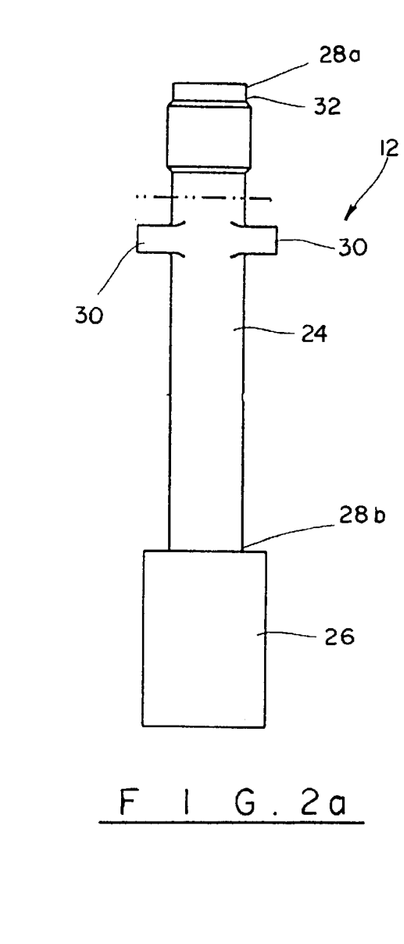
FIG. 2A is a front view of the distractor/guide sleeve assembly shown in FIG. 1.

Referring to FIGS. 2 and 2A, distractor body 12 includes a tubular portion 24 and a hollow rectangular base portion 26 which are integrally formed. Although not shown, windows or openings may be formed in tubular portion 24 or base portion 26 to provide visibility. Tubular portion 24 defines a lumen 28 (FIG. 1) having a first open end 28*a* and a second end 28*b* in communication with hollow base portion 26. A semi-circular rod guide 30 is formed on each side of tubular portion 24. Rod guides 30 are configured to slidably receive and guide distractor rods 18. First end 28*a* of tubular portion 24 includes a series of threads 32 for rotatably receiving dial 14.

Figure 3A:
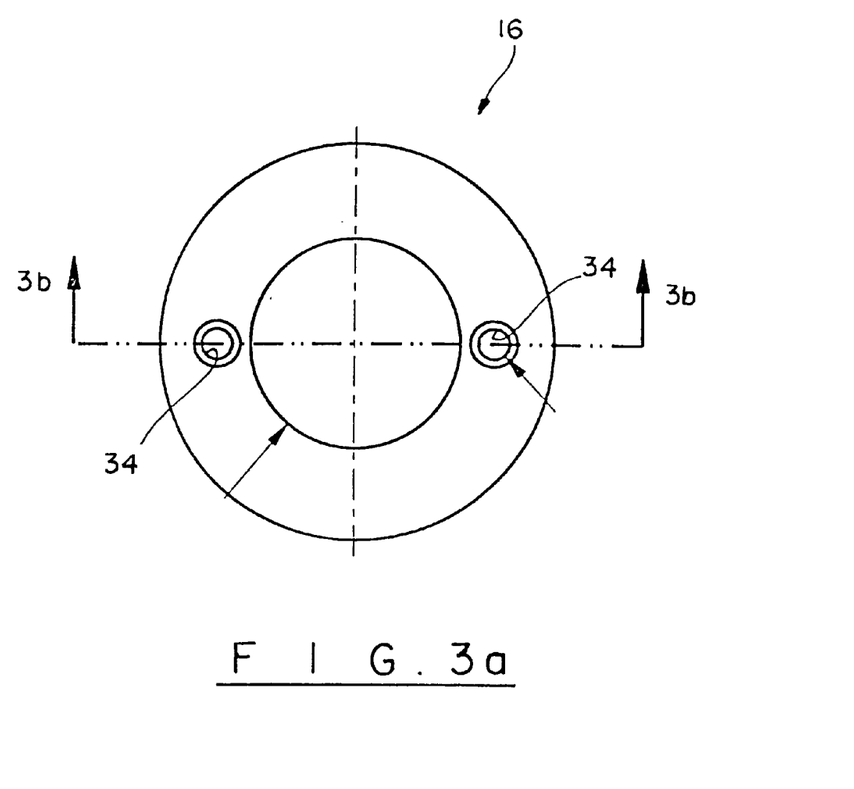
FIG. 3A is a top view of the ring of the distractor/guide sleeve assembly shown in FIG. 1.
Figure 3B:
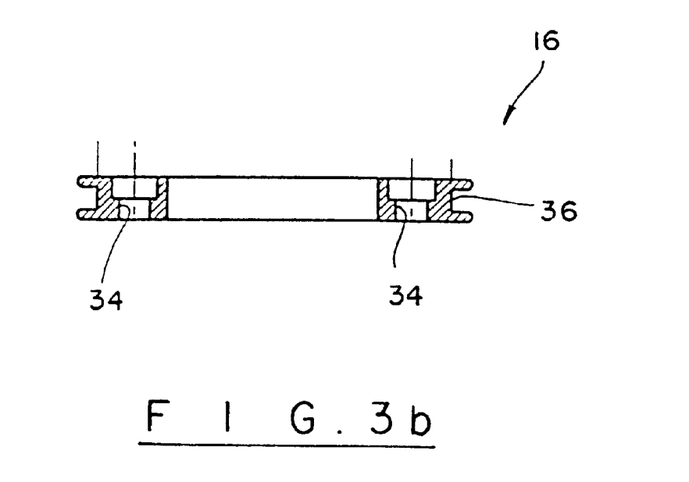
FIG. 3B is a side cross-sectional view of the ring shown in FIG. 3A taken along section lines 3B—3B in FIG. 3A.
Figure 3C:
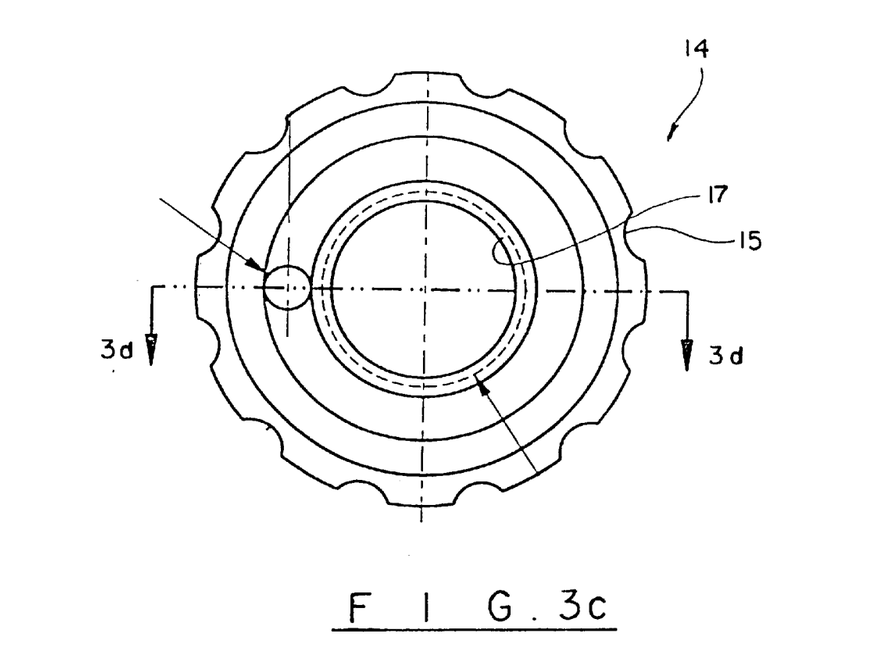
FIG. 3C is a top view of the dial of the distractor/guide sleeve assembly shown in FIG. 1.
Figure 3D:
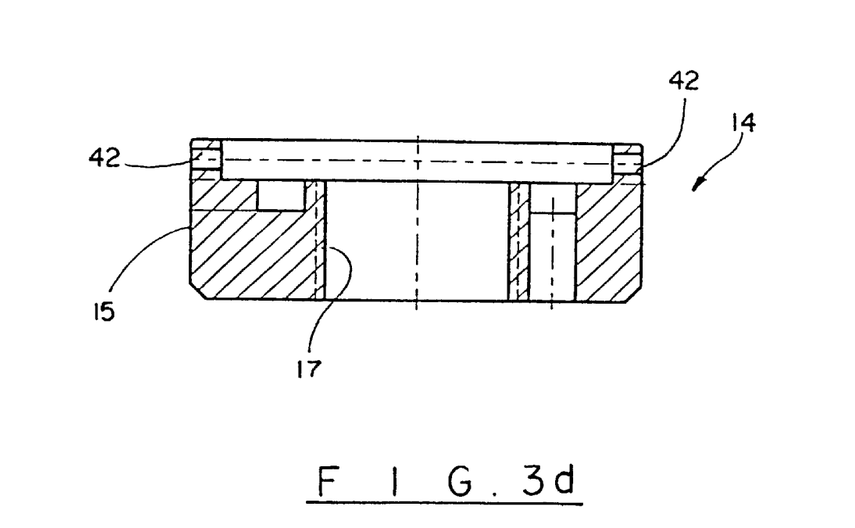
FIG. 3D is a side cross-sectional view of the dial shown in FIG. 3C taken along section lines 3D—3D in FIG. 3C.
Figure 4:
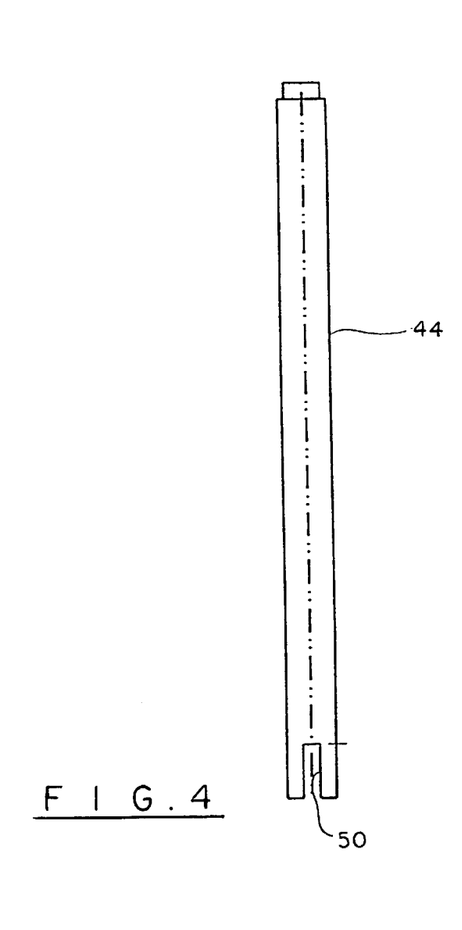
FIG. 4 is a side view of the distractor rod of the distractor/guide sleeve assembly shown in FIG. 1.
Figure 4A:
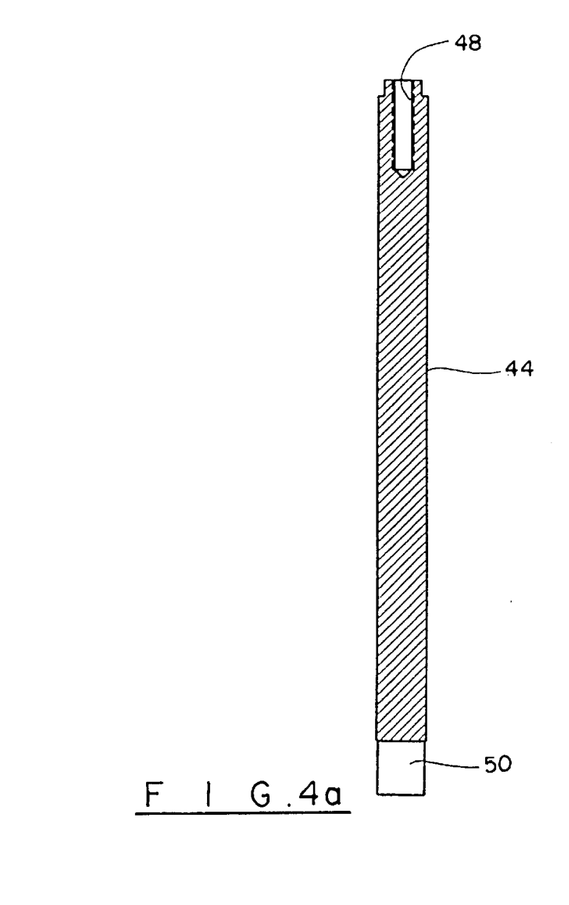
FIG. 4A is a side cross-sectional view of the distractor rod shown in FIG. 4.

Referring to FIGS. 3a and 3b, ring 16 is circular and includes a pair of stepped bores 34 and an annular channel 36 formed thereabout. Stepped bores 34 are dimensioned to receive screws 38 (FIG. 1A) for securing rods 18 to ring 16. Ring 16 is secured within dial 14 (see FIGS. 3c and 3d) with pins 40 (FIG. 1A). Pins 40 extend through openings 42 in dial 14 into annular channel 36 of ring 16 to secure ring 16 within dial 14 while allowing dial 14 to rotate in relation to ring 16. Dial 14 includes a grooved outer surface 15 to facilitate gripping and rotating dial 14. Dial 14 also includes a threaded bore 17 dimensioned to receive threaded first end 28a of body 12.

Referring to FIGS. 4, 4A, 5 and 5A, each distractor rod 18 includes a rod portion 44 and a plate portion 46. Rod portion 44 includes a first end having a threaded bore 48 and a second end having a slot 50 formed therein. Each threaded bore 48 is dimensioned to receive screw 38 (FIG. 1A) to secure the first end of rod portion 44 to ring 16. Each slot 50 of rod portion 44 is configured and dimensioned to slidably receive plate portion 46. Plate portion 46 is frictionally retained within slot 50. Alternately, other retaining means may be used to secure plate portion 46 within slot 50, e.g., screws, adhesives, ultrasonic welding, etc.

Figure 5:
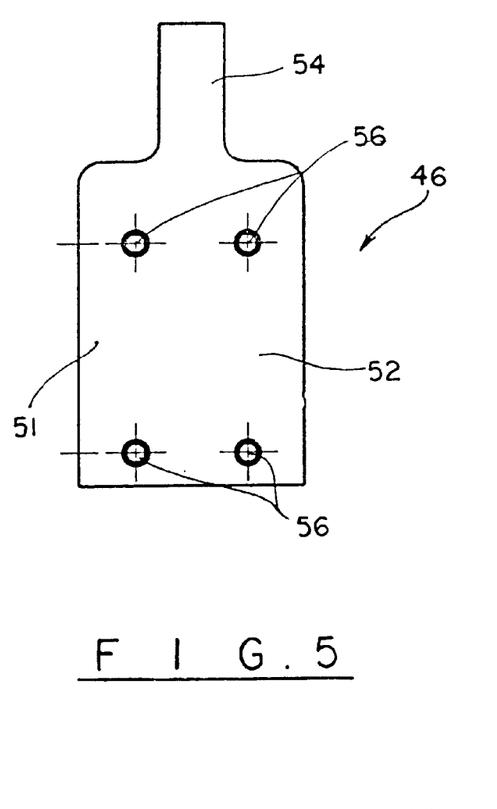
FIG. 5 is side view of one plate portion of the distractor/guide sleeve assembly shown in FIG. 1.
Figure 5A:
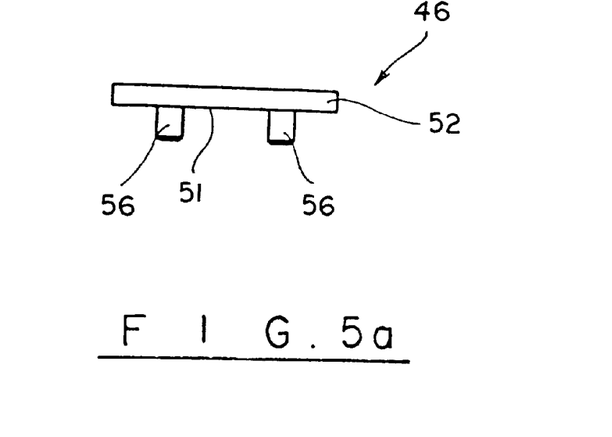
FIG. 5A is a top view of the plate portion shown in FIG. 5.

Plate portion 46 includes a paddle section 52 and a handle section 54. Handle section 54 is dimensioned to be received in slot 50 of rod portion 44. Paddle section 52 includes a flat base 51 having a plurality of cam members 56 extending therefrom. Cam members 56 will be described in further detail below.

Figure 6:
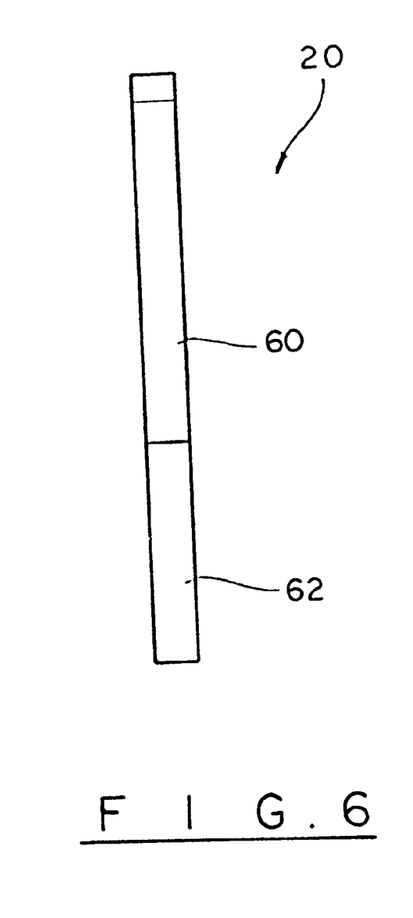
FIG. 6 is a side view of one jaw of the distractor/guide sleeve assembly shown in FIG. 1.
Figure 6A:
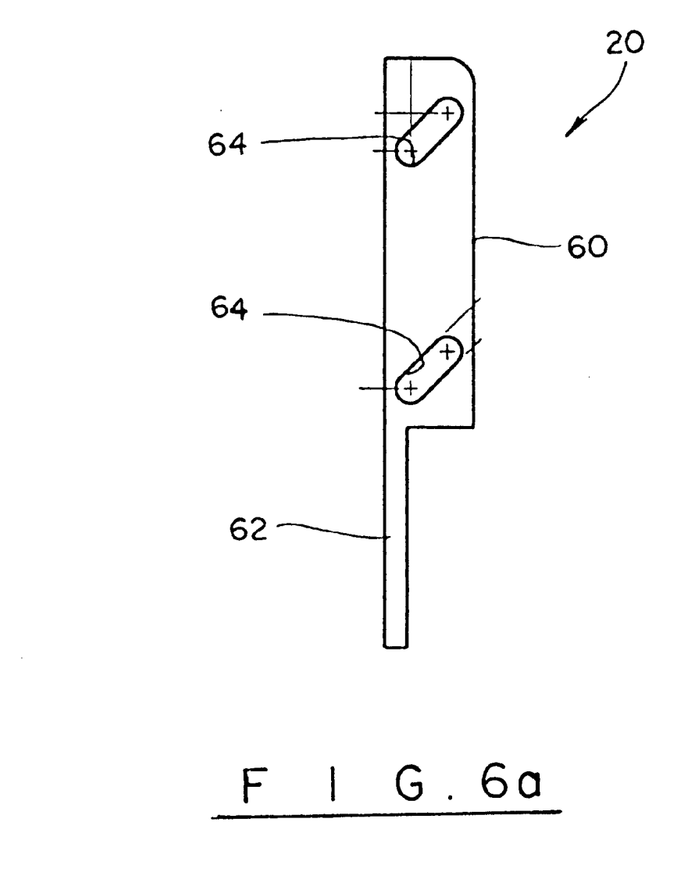
FIG. 6A is a front view of the jaw shown in FIG. 6.

Referring to FIGS. 6 and 6A, each jaw 20 of the two pair of jaws 20a and 20b includes a body 60 having a distally extending finger 62. Body 60 includes one or more cam slots 64 formed therein. Preferably body 60 includes two cam slots, although three or more may be provided. Alternately, only a single cam slot need be provided. Cam slots 64 are dimensioned to receive cam members 56 formed on plate portion 46 of distractor rods 18. Alternately, only a single pair of jaws need be provided on the distractor/guide sleeve. Such an embodiment would also require only a single distractor rod and cover plate.

Figure 7:
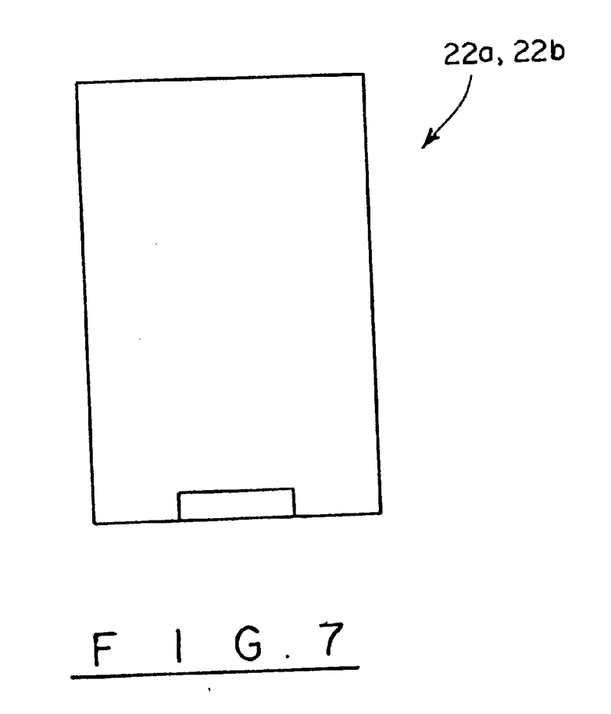
FIG. 7 is a front view of one cover plate of the distractor/guide sleeve assembly shown in FIG. 1.
Figure 7A:
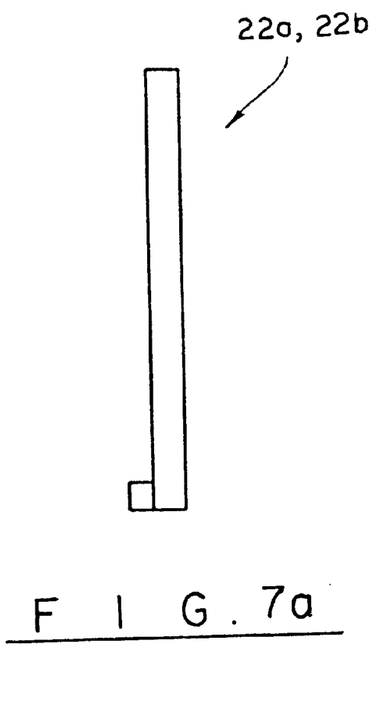
FIG. 7A is a side view of the cover plate shown in FIG. 7.

Referring to FIGS. 7 and 7A cover plates 22a and 22b are secured to open sides of base portion 26 to retain jaws 20 and plate portion 46 of distractor rods 18 in engagement. Cover plates 22a and 22b may snap fit to base portion 26 or other attachment means may be provided, e.g., screws, welding, adhesives, etc.

In operation, when dial 14 is rotated in a clockwise direction on the threaded end of body 12, dial 14 advances ring 16 towards the second end of body 12. Movement of ring 16 advances distractor rods 18 in a direction parallel to the longitudinal axis of body 12, thus advancing cam members 56 in a direction parallel to the longitudinal axis of body 12. As cam members 56 move in relation to cam slots 64, each jaw 20 of each pair of jaws 20a and 20b is urged outward away from the longitudinal axis of body 12 to increase the spacing between the fingers 62 of each pair of jaws 20a and 20b. When dial 14 is rotated in a counter-clockwise direction, rods 18 are retracted to decrease the spacing between each of fingers 62 of each pair of jaws 20a and 20b in a manner similar to that described above.

The above described distractor/guide sleeve may be used to distract adjacent vertebrae during spinal surgery, e.g., a cervical spinal fusion procedure. The distractor body including the tubular portion and the base portion function as a guide for the surgical instruments used during the surgical procedure, e.g., reamers, taps, insertion tool, etc. Once the guide sleeve has been parked in the intervertebral space, with fingers 62 positioned between adjacent vertebrae, dial 14 can be rotated to distract the adjacent vertebrae. It is no longer necessary to relocate the proper graft bed after each time a surgical instrument is used, since the distractor/guide sleeve is secured in a fixed location with respect to the graft bed during the entire procedure. Moreover, the presently disclosed jaw structure provides a sturdy structure which minimizes wobbling which may occur while using the surgical instruments.

Figures 8, 9:
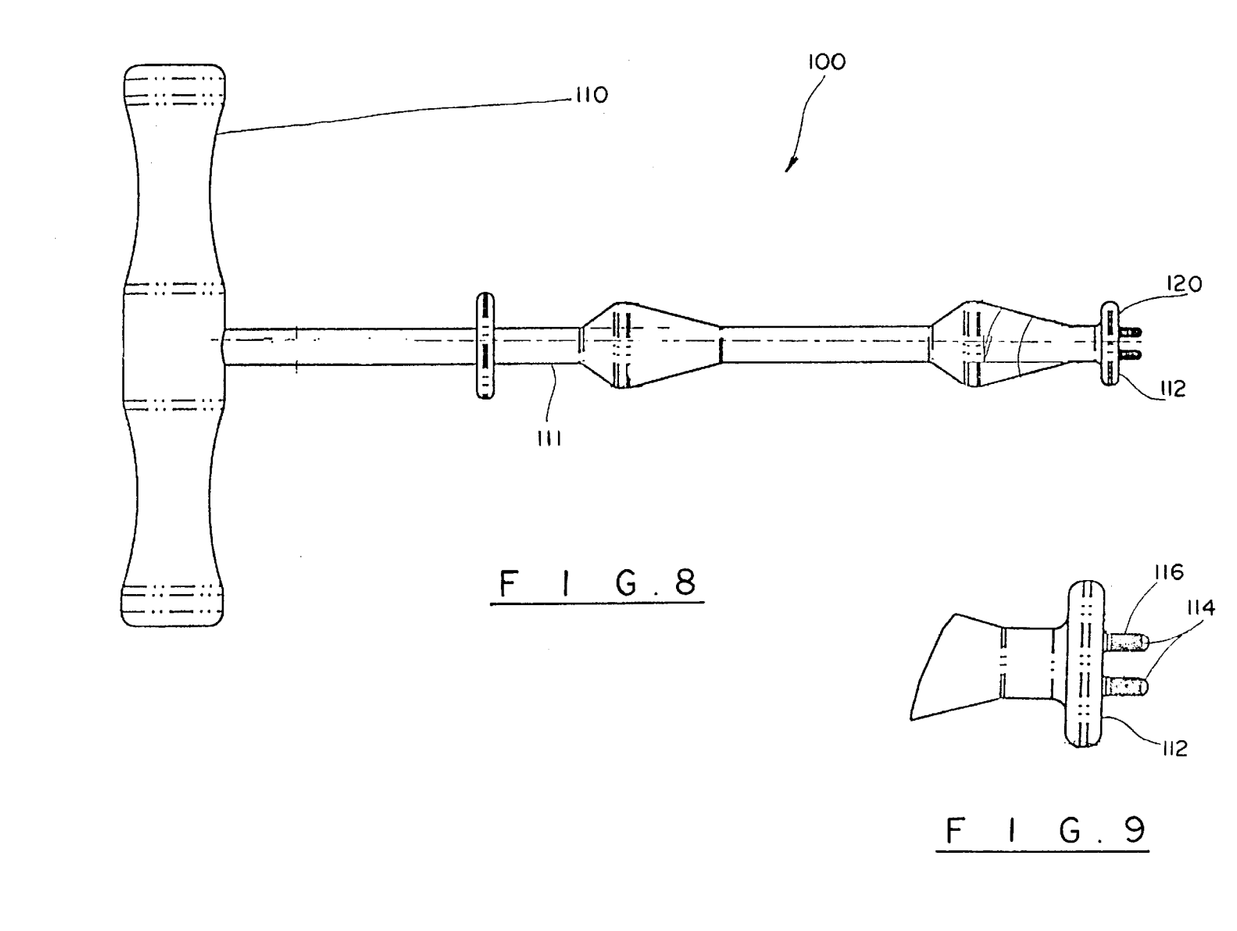
FIG. 8 is a front view of one preferred embodiment of the presently disclosed implant insertion tool.
FIG. 9 is a front view of the distal end of the insertion tool shown in FIG. 8.

FIGS. 8 and 9 illustrate an insertion tool, shown generally as 100, for inserting a thread implant into an implant receiving bed. Insertion tool 10 includes a handle 110, an elongated shaft 11 and an implant engaging structure 120. Implant engaging structure 120 is secured to or formed integrally with elongated shaft 111 and includes a base member 112 and a pair of protrusions or prongs 114. Base member 112 includes a flat face which abuts the trailing end of an implant when the implant is supported on the insertion tool. Protrusions 114 have an outer surface 116 which is at least partially roughened. The roughened surface may include ridges, knurling, dimples or any other slip resistant surface.

Figure 10:
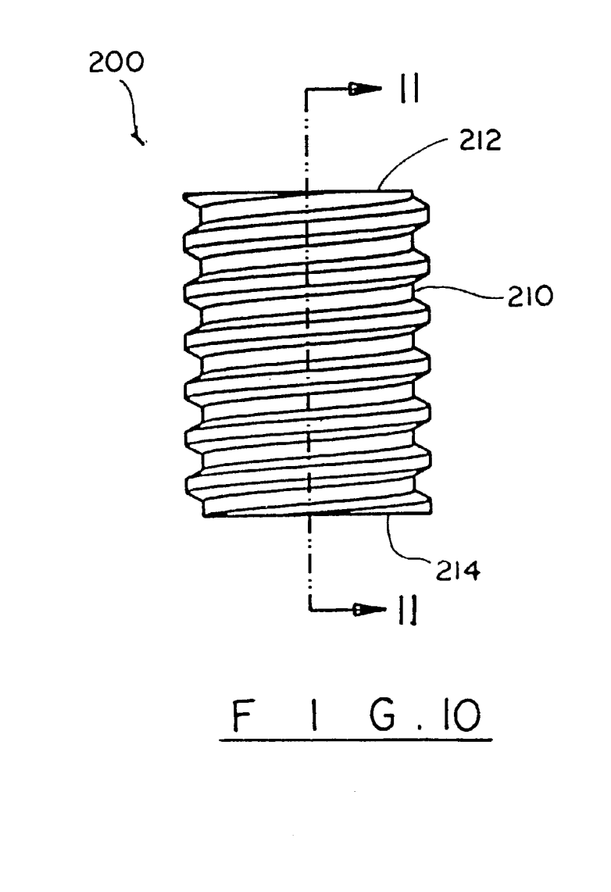
FIG. 10 is a side view of one preferred embodiment of the presently disclosed implant.
Figure 11:
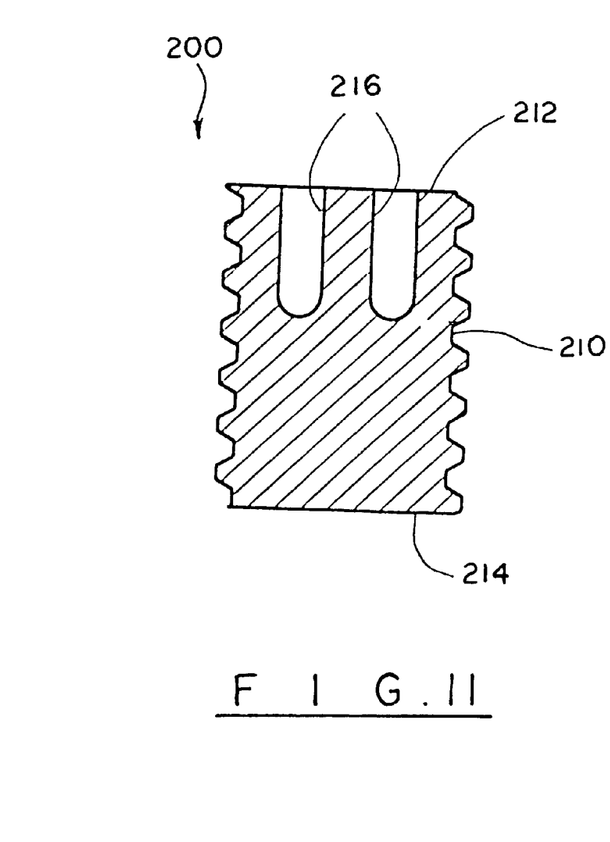
FIG. 11 is a side cross-sectional view of the implant shown in FIG. 10 taken along section lines 11—11 in FIG. 10

FIGS. 10 and 11 illustrate an implant 200 having a cylindrical threaded body 210 and top and bottom surfaces 212 and 214. Implant 200 is constructed from a biocompatible material. Preferably, implant 200 is formed from cortical or cancellous bone. Top surface 212 includes a pair of substantially cylindrical bores 216 formed therein. Bores 216 are positioned to receive protrusions 114 (FIG. 9) and have an inside diameter substantially equal to the outside diameter of protrusions 114. When protrusions 114 are pressed into bores 216, roughened outer surface 116 of protrusions 114 prevent implant 200 from separating from engaging structure 120 without applying additional force to implant 200.

In use, after implant 200 has been positioned on engaging structure 120 of insertion tool 100, handle 110 can be manipulated to thread implant 200 into a previously prepared receiving bed, e.g., a tapped bore formed between adjacent vertebrae during a spinal fusion surgical procedure. Thereafter, insertion tool 100 can be pulled rearwardly with a force sufficient to overcome the frictional engagement between protrusions 114 and bores 26 to separate the implant from the insertion tool.

It will be understood that various modifications may be made to the embodiments disclosed herein. For example, any materials having the requisite strength requirements which are suitable for surgical use may be used to construct the distractor/guide sleeve assembly and insertion tool including surgical grade stainless steel, plastics, etc. Moreover, the size of the distractor/guide sleeve may be changed to suit a particular surgical procedure, e.g., cervical spinal fusion, lumbar spinal fusion, thoracic spinal fusion, etc. Therefore, the above description should not be construed as limiting, but merely as exemplifications of preferred embodiments. Those skilled in the art will envision other modifications within the scope and spirit of this disclosure.

What is claimed is:

1. A distractor comprising:
    a body extending along a longitudinal axis;
    an elongated first jaw and an elongated second jaw mounted on a distal end of the body and configured to extend into an intervertebral space; and
    an actuator mounted on a proximal end of the body and operative to generate an axial force exerted upon the first and second elongated jaws so that when the axial force is directed to the distal end, the first and second elongated jaws move relative to one another and transversely to the longitudinal axis from an approximated position to a distracted position.

2. The distractor of claim 1, wherein the actuator includes a dial and a distractor rod extending between and coupled to the dial and to the first and second elongated jaws, the dial being operative to axially displace the distractor rod so that when the rod moves axially towards the distal end, the first and second jaws are displaced laterally outwards from the longitudinal axis in opposite directions to the distracted position.

3. The distractor of claim 2, wherein the first and second elongated jaws each have a respective slot provided with a cam surface extending angularly towards the longitudinal axis and being in sliding contact with the distractor rod.

4. The distractor of claim 2, wherein the dial is threadedly mounted on the body to rotate thereabout while being axially displaceable along the body.

5. The distractor of claim 1, wherein the axial force is directed towards the proximal end, the first and second elongated jaws move laterally inwards from the distracted position to the approximated position.

6. A distractor and guide sleeve assembly comprising:
   a elongated body having one and other opposite ends defining therebetween a guide channel dimensioned to slidably receive an implant;
   at least one pair of jaws supported on the one end of the elongated body, the at least one pair of jaws being configured to extend into an inervertebral space between adjacent vertebrae and being movable in relation to each other between approximated and distracted positions; and
   an actuator supported on the other end of the elongated body, the actuator being operably connected to the at least one pair of jaws and being movable along the elongated body towards the one end thereof to move the at least one pair of jaws from the approximated to distracted positions.

7. A distractor and guide sleeve assembly according to claim 6, wherein the at least one pair of jaws includes two pairs of jaws.

8. A distractor and guide sleeve assembly according to claim 6, wherein the actuator includes a rotatable dial.

9. A distractor and guide sleeve assembly comprising:
   a body defining a guide channel dimensioned to slidably receive an implant and extending along a longitudinal axis;
   at least one pair of jaws supported on one end of the body, the at least one pair of jaws being configured to extend into an inervertebral space between adjacent vertebrae and being movable in relation to each other between approximated and distracted positions; and
   a dial supported on another end of the body and rotatable about the longitudinal axis; and
   at least one elongated distractor rod having one end operably associated with the dial and a second end operably associated with the at least one pair of jaws, the at least one distractor rod being axially displaceable in response to the rotation of the dial to move the at least one pair of jaws between the approximated and distracted positions.

10. A distractor and guide sleeve assembly according to claim 9, wherein the second end of the at least one distractor rod includes a plurality of cam members configured to be slidably received in cam slots formed in each jaw of the at least one pair of jaws, the cam members being moveable in relation to the cam slots to effect movement of the at least one pair of jaws between the approximated and distracted positions.

11. A distractor and guide sleeve assembly according to claim 10, wherein the at least one pair of jaws includes two pairs of jaws and the at least one distractor rod includes two distractor rods.

* * * * *